(12) United States Patent
O'Donald et al.

(10) Patent No.: US 12,232,788 B2
(45) Date of Patent: Feb. 25, 2025

(54) BONE FIXATION SYSTEM

(71) Applicant: OSO Extremity, Inc., Nederland, TX (US)

(72) Inventors: Pete O'Donald, Port Arthur, TX (US); Mickey Stapp, Martinez, GA (US)

(73) Assignee: OSO EXTREMITY, INC., Nederland, TX (US)

( * ) Notice: Subject to any disclaimer, the term of this patent is extended or adjusted under 35 U.S.C. 154(b) by 262 days.

(21) Appl. No.: 17/899,335

(22) Filed: Aug. 30, 2022

(65) Prior Publication Data

US 2022/0409252 A1 Dec. 29, 2022

Related U.S. Application Data

(63) Continuation of application No. 16/525,396, filed on Jul. 29, 2019, now Pat. No. 11,432,860.

(60) Provisional application No. 62/711,755, filed on Jul. 30, 2018.

(51) Int. Cl.
| | | |
|---|---|---|
| *A61B 17/86* | (2006.01) | |
| *A61B 17/84* | (2006.01) | |
| *A61B 17/88* | (2006.01) | |
| *A61B 17/72* | (2006.01) | |

(52) U.S. Cl.
CPC .......... *A61B 17/848* (2013.01); *A61B 17/842* (2013.01); *A61B 17/8861* (2013.01); *A61B 17/725* (2013.01); *A61B 17/7291* (2013.01); *A61B 17/86* (2013.01); *A61B 2017/8655* (2013.01)

(58) Field of Classification Search
CPC .............. A61B 17/725; A61B 17/7225; A61B 17/7233; A61B 17/7291; A61B 17/842; A61B 17/848; A61B 17/846; A61B 17/86; A61B 17/8861; A61B 2017/8655
USPC ..... 606/62, 63, 67, 301, 302, 304, 305, 306, 606/307, 308, 318, 319, 320, 321, 322, 606/323, 328, 103, 105
See application file for complete search history.

(56) References Cited

U.S. PATENT DOCUMENTS

| | | | | |
|---|---|---|---|---|
| 2,398,915 A | * | 4/1946 | Bell ..................... | A61B 17/685 606/328 |
| 7,207,995 B1 | * | 4/2007 | Vandewalle ....... | A61B 17/8875 606/104 |
| 7,473,256 B2 | * | 1/2009 | Assell ................ | A61B 17/1757 606/90 |
| 2009/0306718 A1 | * | 12/2009 | Tipirneni ........... | A61B 17/8685 606/264 |
| 2013/0079776 A1 | * | 3/2013 | Zwirkoski ............ | A61B 17/683 606/62 |
| 2016/0338746 A1 | * | 11/2016 | Scruggs ............... | A61B 17/725 |

* cited by examiner

*Primary Examiner* — Eduardo C Robert
*Assistant Examiner* — David C Comstock
(74) *Attorney, Agent, or Firm* — David Meibos; Maywood IP Law

(57) ABSTRACT

A system and method for osseous fixation is a surgical hardware device that allows bone fixation for purposes of fracture repair, arthrodesis, or other types of orthopedic applications. A partially threaded wire or pin is inserted into the bone and external compression and rotational stability are achieved with a locking cap. The locking cap may include serrations or other anti-rotation features which engage bone to provide rotational stability. Upon adequate bone healing, the external cap may be used to facilitate removal of the wire/pin from the bone.

20 Claims, 6 Drawing Sheets

BONE FIXATION SYSTEM

CROSS-REFERENCE TO RELATED APPLICATIONS

The present application is a continuation of U.S. patent application Ser. No. 16/525,396 filed on Jul. 29, 2019 entitled "Bone Fixation System", which claims the priority benefit of U.S. Provisional Application Ser. No. 62/711,755, entitled "Locking Pin Cap For Osseus Fixation", which was filed on Jul. 30, 2018. The foregoing is incorporated by reference as though set forth herein in its entirety.

TECHNICAL FIELD

This disclosure relates to locking mechanisms for use with k-wires and other orthopedic devices. In some embodiments, the disclosed systems and associated methods are used with k-wires for fixation of a first bone portion relative to a second bone portion.

BACKGROUND

Wire or pin fixation has been a popular form of fixation for many surgical procedures such as small bone fractures and small joint arthrodesis. Many surgeons prefer this technique due to its relatively simple application and fair results. However, simple, single Kirschner wire (k-wire) or pin fixation alone does not provide compression or rotational control. The most common complications with traditional wire or pin fixation are nonunion and malunion due to lack of compressions and excess motion; most commonly due to rotation about the long axis of the wire or pin. Screw fixation devices for small bone fractures are often too large to address small fracture fragments. Intra-articular implants used for small joint arthrodesis are expensive and require complex implantation compared to wire or pin fixation. Removal of screws or intra-articular implants can be costly and complicated in the event of failure or infection.

SUMMARY OF THE DISCLOSURE

The various systems and methods of the present disclosure have been developed in response to the present state of the art, and in particular, in response to the problems and needs in the art that have not yet been fully solved by currently available methods and technology. The systems and methods of the present disclosure may provide compression and greater rotational stability during osseous fixation of one bone portion relative to a second bone portion and may provide increased ability to repair small fractures with fewer complications.

More specifically, the bone fixation system disclosed herein may be a surgical hardware system that allows bone fixation for purposes of fracture repair, arthrodesis, or many other types of orthopedic applications. The system may provide both compression and anti-rotation features to promote osseous union. This system can be used to fixate very small bone fracture fragments or digital repair without further fracturing or creation of stress risers often seen with screw fixation. The systems and procedures disclosed herein may provide improved compression and/or rotational stability for small joint arthrodesis or small bone fractures leading to improved surgical outcomes.

To achieve the foregoing, and in accordance with the disclosure as embodied and broadly described herein, a first aspect of the disclosure includes a cap with a body portion and a stem portion. The cap may further have a first bore and a second bore transverse to, and in communication with, the first bore. A wire may be insertable through the first and second bone portions; the wire may have a first end and a threaded second end anchorable in the second bone portion. The first end of the wire may be slidably receivable within the first bore of the cap and the cap may be movable along wire toward the threaded second end of the wire to decrease a distance between the cap and the threaded second end of the wire. A set screw may be receivable in the second bore of the cap; the set screw may be actuable to contact the wire to fix a position of the wire within the first bore.

In an embodiment, the threaded second end of the wire tapers to a point.

In an embodiment, the stem portion of the cap includes one or more anti-rotation features that contact the first bone portion in response to pressure urging the cap against the first bone portion to prevent rotation of the cap.

In an embodiment, the cap is cylindrical, and a first outer diameter of the body portion is greater than a second outer diameter of the stem portion.

In an embodiment, the body portion and the stem portion of the cap are separated by a chamfered portion.

In an embodiment, the first bore extends lengthwise within the cap through the body portion and the stem portion.

In an embodiment, the second bore extends transversely through the body portion of the cap.

In an embodiment, when the wire is inserted through the first and second bone portions, the threaded second end of the wire is anchored in the second bone portion, and the cap is moved toward the threaded second end of the wire to abut the first bone portion, the system restricts motion of a joint or fracture between the first and second bone portions.

A second aspect of the disclosure includes a method for fixation of a first bone portion relative to a second bone portion through use of a system including a wire, a cap, and a set screw. The method may include inserting the wire percutaneously through a skin and subcutaneous tissue portion, through the first bone portion and into the second bone portion, the wire having a first end, and a threaded second end; anchoring the threaded second end of the wire in the second bone portion; placing the cap onto the first end of the wire such that the wire is slidably received in a first bore of the cap, wherein the cap further includes a body portion, a stem portion, and a second bore transverse to, and in communication with, the first bore; moving the cap along the wire toward the threaded second end of the wire to decrease a distance between the cap and the threaded second end of the wire, and to compress the cap against the first bone portion; actuating the set screw within in the second bore, to contact the wire and fix a position of the wire relative to the cap within the first bore; and removing the system after osseous union of the first bone portion to the second bone portion has occurred.

In an embodiment, the threaded second end of the wire tapers to a point.

In an embodiment, the method further includes sliding the cap along the wire to abut the first bone portion.

In an embodiment, the stem portion of the cap includes one or more anti-rotation features, and the method further includes anchoring the one or more anti-rotation features on the first bone portion to prevent rotation of the cap relative to the first bone portion.

In an embodiment, sliding the cap along the wire to abut the first bone portion includes inserting the stem portion of the cap percutaneously into the skin and subcutaneous tissue portion via an incision to abut the first bone portion.

In an embodiment, inserting the stem portion of the cap percutaneously into the skin and subcutaneous tissue portion includes leaving the body portion of the cap outside of the skin and subcutaneous tissue portion.

In an embodiment, the cap further includes a chamfered portion which separates the body portion and the stem portion, and inserting the stem portion of the cap percutaneously into the skin and subcutaneous tissue portion includes causing the chamfered portion to reside outside the skin when the stem portion of the cap abuts the first bone portion.

A third aspect of the disclosure includes a method for removing a system for fixation of a first bone portion relative to a second bone portion, wherein the system is implanted percutaneously to extend through a skin and subcutaneous tissue portion via an incision, and into the second bone portion to restrict motion of a joint or fracture between the first and second bone portions to allow osseous union between the first and second bone portions. The method may include: making an incision into the skin and subcutaneous tissue portion adjacent to the system, the system including a cap with a body portion and a stem portion, the cap further having a first bore and a second bore transverse to, and in communication with, the first bore; a wire slidably received within the first bore of the cap and having a threaded end anchored in the second bone portion; and a set screw received in the second bore of the cap which is actuable to fix a position of the wire within the first bore; loosening the set screw within the second bore of the cap to release the position of the wire within the first bore; removing the cap from the wire and the skin and subcutaneous tissue portion; removing the threaded end of the wire from the second bone portion; and withdrawing the wire from the skin and subcutaneous tissue portion.

In an embodiment, the stem portion of the cap includes one or more anti-rotation features anchored on the first bone portion to prevent rotation of the cap, and removing the cap from the wire further includes dislodging the one or more anti-rotation features from the first bone portion.

In an embodiment, the body portion of the cap remains outside of the skin and subcutaneous tissue portion and the first and second bone portions during osseous union between the first and second bone portions, and removing the cap from the wire and the skin and subcutaneous tissue portion includes grasping the cap from outside the skin and subcutaneous tissue portion.

In an embodiment, the cap further includes a chamfered portion which separates the body portion and the stem portion. Prior to removal, the chamfered portion may reside outside the skin and subcutaneous tissue portion, the stem portion of the cap may abut the first bone portion, and the body portion of the cap may remain outside of the skin and subcutaneous tissue portion during osseous union between the first and second bone portions. Removing the cap from the wire and the skin and subcutaneous tissue portion may include withdrawing the stem portion from the skin.

In an embodiment, the threaded end of the wire tapers to a point.

These and other features and advantages of the present disclosure will become more fully apparent from the following description and appended claims, or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the claims of the present disclosure, the exemplary embodiments of the disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 8, is not intended to limit the scope of the appended claims, but is merely representative exemplary of exemplary embodiments of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
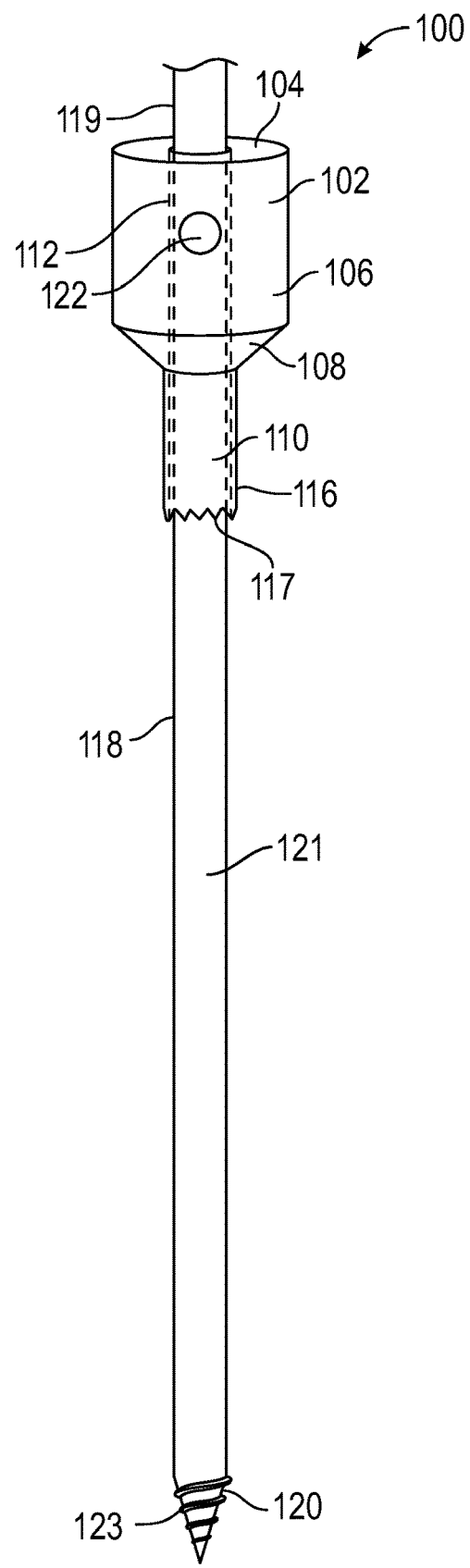
FIG. 1 is an exterior view of a bone fixation system according to one embodiment, the system including a locking cap and a wire.
Figure 2:
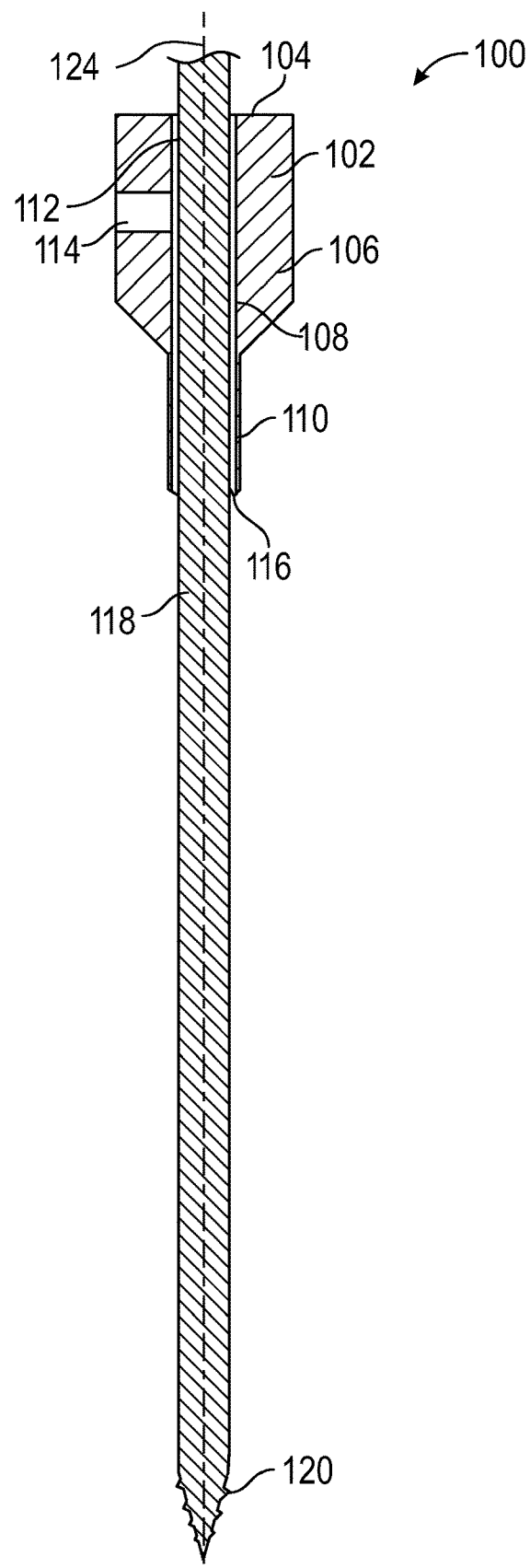
FIG. 2 is a longitudinal cross-sectional view of FIG. 1 showing the placement of two bores and features of the wire as well as how the bores interact with the wire portion of the system.

Referring to FIGS. 1 and 2, an exterior view and a cross-sectional view illustrate an osseous fixation system 100 according to one embodiment of the disclosure. System 100 comprises a locking cap 102, a wire 118, and a set screw 122. In this system 100, the wire may be extended through one or more bone portions and anchored in a bone portion. The cap is mounted on the wire 118 and moved along the wire 118 toward the bone portions to compress the bone portions together. The set screw 122 is actuated to lock the position of the locking cap 102 on the wire 118 to restrict motion and maintain compression and stability until osseous fixation occurs.

Figure 3:
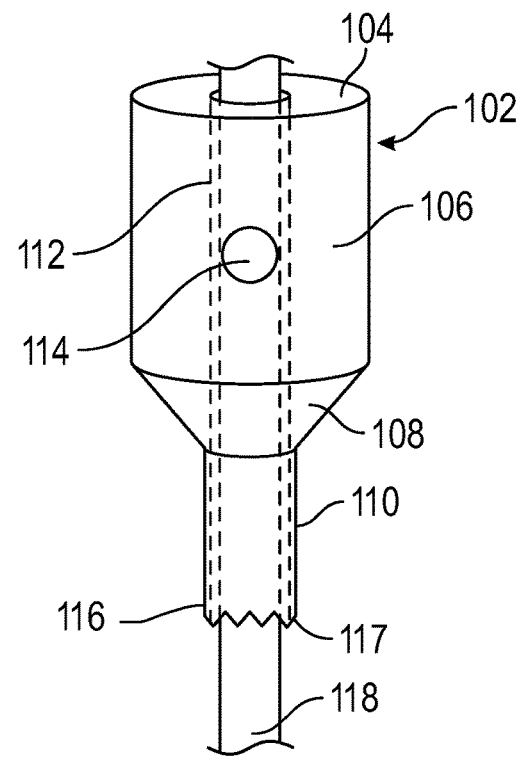
FIG. 3 is a detailed exterior view of the locking cap illustrating the bore positions and an anti-rotation feature of the second end of the cap.
Figure 4:
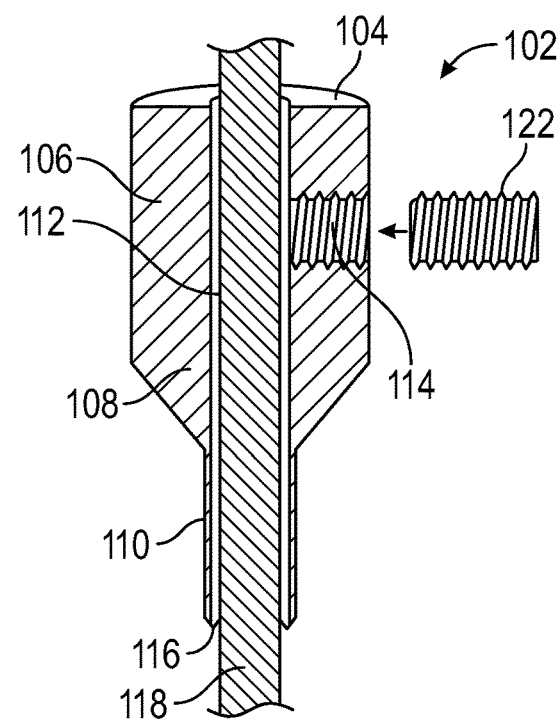
FIG. 4 is a longitudinal cross-sectional view of the locking cap illustrated in FIG. 3, further including a set screw.
Figure 5:
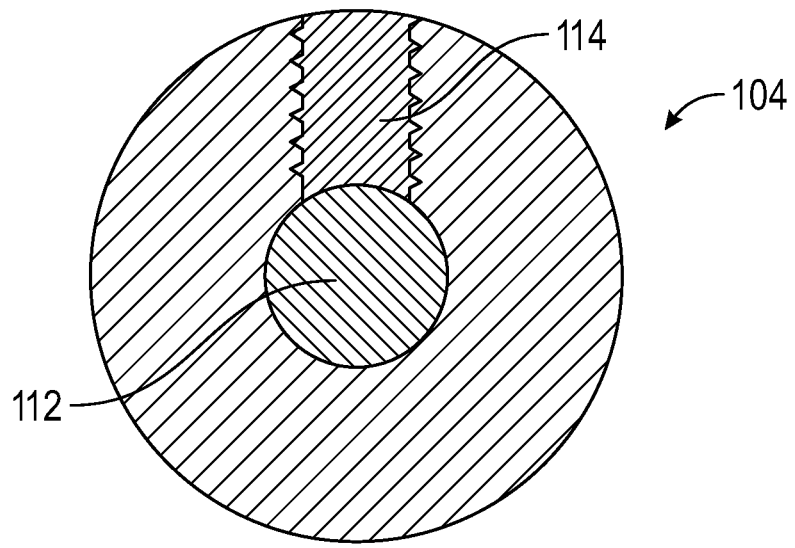
FIG. 5 is a top down transverse cross-sectional view of the locking cap illustrating placements of the first bore and the second bore in relation to each other.
Figure 6:
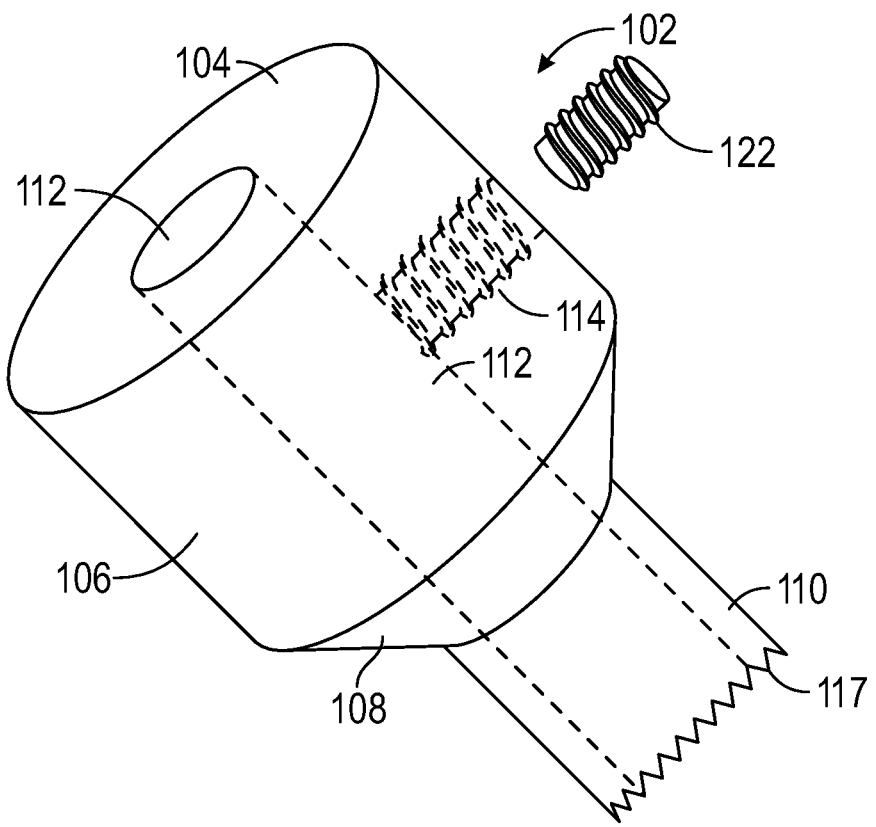
FIG. 6 is an isometric view of the locking cap highlighting the structure of the locking cap including the first bore, the second bore, the anti-rotation feature, and set screw placement.

FIGS. 3 and 4 show one embodiment of the locking cap 102. The locking cap 102 extends between a first end 104 and a second end 116. The locking cap 102 includes a body portion 106, a chamfered portion 108, and a stem portion 110 that terminates at the second end 116. The locking cap 102 can include one or more anti-rotation features 117, which may optionally be serrations, as depicted. A first bore 112 extends the length of the locking cap 102, coaxial with a system longitudinal axis 124. A second bore 114 is transverse to and in communication with the first bore 112, and may be threaded to accommodate the set screw 122 or similar device used to secure or lock the wire 118 in place within the first bore 112. In another embodiment, the first bore 112 may be offset from the system longitudinal axis 124, and/or the second bore 114 may be at an angle other than perpendicular relative to the first bore 112. In other embodiments, there may be additional bores (not shown) housing additional securing devices.

As shown in FIGS. 3 and 4, the anti-rotation feature 117 may be located at the second end 116 of the locking cap 102. The anti-rotation feature 117 may contact one bone fragment or bone portion in response to pressure, becoming engaged with or embedded in the bone portion, and preventing rotation of the locking cap 102 in relation to the bone portion. The anti-rotation feature 117 may be one or more serrations as shown in this embodiment, but it may additionally or alternatively comprise one or more spikes, teeth, pins, surface roughening, or other denticulated features.

The wire 118 includes a first end 119 which may be a free end, a shaft 121, and a second end 120. The second end 120 may be tapered to a point and may include threads 123. As shown in at least FIGS. 2 and 7, the tapered threaded portion of the wire 118 has a smaller outer diameter than the outer diameter of the shaft 121. This may result in easier withdrawal of the wire from bone. Optionally, the tapered threaded portion of the wire 118 may have threading that is designed such that the threads protrude only very little, or do not protrude at all, beyond the diameter of the shaft 121. The overall length of the wire 118 may vary as needed.

The embodiment of the locking cap 102 of FIGS. 3-6 is shaped as a cylinder, having a circular first end 104. Other embodiments of the locking cap 102 may embody other elongated body shapes, and have a first end which is non-circular, for example rectangular, triangular, oval, octagonal or hexagonal, among others. The elongated body shape may be radially symmetrical or asymmetrical or may have radially symmetrical and radially asymmetrical portions.

In the embodiment depicted, the chamfered portion 108 is tapered, reducing the diameter of the body portion 106 to the diameter of the stem portion 110. The chamfered portion 108 may be constantly tapered as shown but can take many forms including but not limited to an abrupt shoulder, or variable angles of reduction. The body portion 106 is sufficiently wide to accommodate the second bore 114 and set screw 122, while the reduced width of the narrower stem portion 110 may allow for easier insertion and/or reduced discomfort and wound size when the stem portion 110 is inserted into skin and subcutaneous tissue during use.

The locking cap 102 may be made from one or more polymeric, metal, and/or ceramic materials through any suitable manufacturing methods including, but not limited to, injection molding, milling, casting, forging, or an additive manufacturing process (e.g., 3D printing). In one embodiment, the entire length of the locking cap 102 may be 17 mm, with the body portion 106 being 10 mm in outer diameter and 10 mm in length from the first end 104 to the chamfered portion 108. The chamfered portion 108 may be tapered or otherwise reduce the body 106 outer diameter from 10 mm to the stem portion 110 outer diameter of 3 mm, with the chamfered portion 108 and the stem portion 110 having a combined length of 7 mm. The first bore 112 in this embodiment has a diameter of 1.5 mm running through the length of the locking cap 102. The second bore 114 may be sized to receive a #3 set screw. In other embodiments, the system 100 and locking cap 102 may have dimensions greater than or less than those given for this embodiment, in order to accommodate individual needs. Similarly, variously sized set screws and/or wires may be employed to provide for systems having a variety of sizes. In other embodiments of the system, the wire 118 may be a line, cable, pin, thread, rod, or other longitudinally elongated body.

Figure 7:
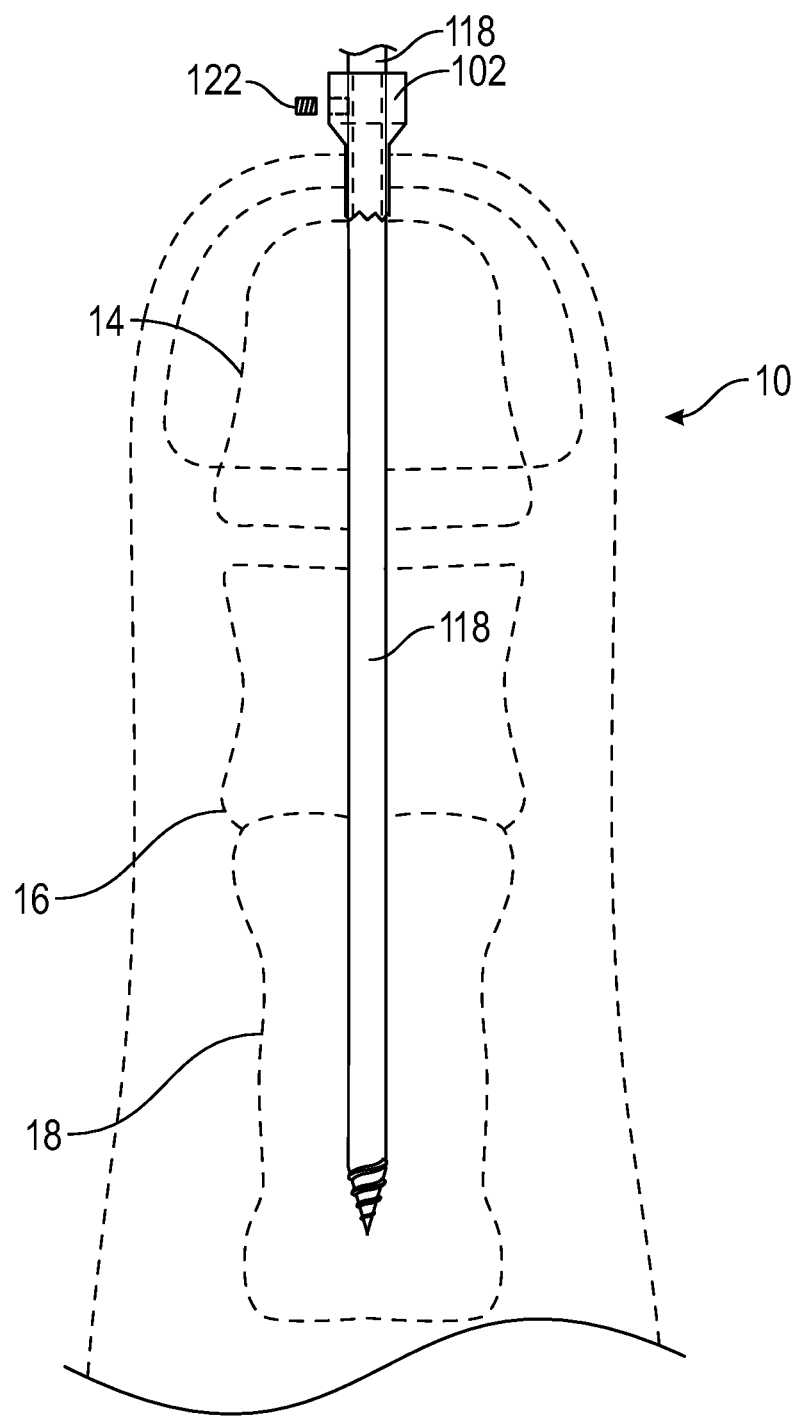
FIG. 7 is schematic of the bone fixation system and the placement of the system in relation to the anatomy of a toe, with the locking cap placed at the distal end of the toe and the wire extending through the bones of the toe with the threaded end anchored in the proximal phalanx.
Figure 8:
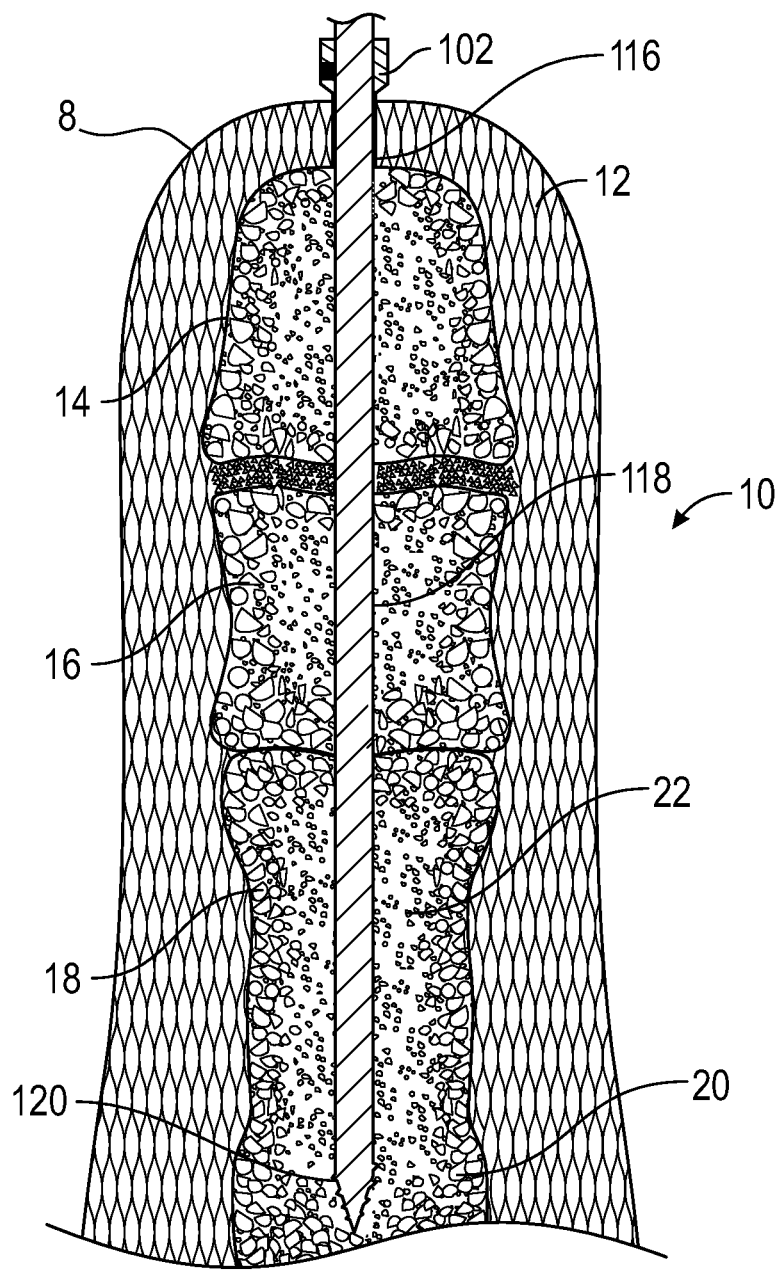
FIG. 8 is a longitudinal cross-sectional view of FIG. 7 illustrating how the bone fixation system interacts with the tissue and bone structure of the toe.

FIGS. 7-8 illustrate a method of use of the system 100. FIG. 7 shows an external view of system 100 being used for fixation of one bone portion to a second bone portion, in this case for fixation between bones of a toe, FIG. 8 shows a detailed cross-sectional view of FIG. 7. A method of use of system 100 for fixation of a first bone portion (for example, a middle phalanx 16) relative to a second bone portion (for example, a proximal phalanx 18) may include one or more of the following steps: the wire 118 is inserted percutaneously via an incision through skin 8, subcutaneous tissue 12, and through medullary 22 and cortical 20 bone layers of the distal phalanx 14, a middle phalanx 16, and into the proximal phalanx 18. The threaded second end 120 is anchored in subchondral cortical bone 20 of the proximal phalanx 18. The threaded second end 120 may, in some embodiments, be anchored within the interior of the proximal phalanx 18, in cancellous bone. However, inserting the threaded second end 120 sufficiently far to reach the cortical bone toward the proximal end of the proximal phalanx 18 may provide for more secure anchorage, and may reduce the likelihood of the threaded second end 120 moving (for example, by pulling free of the bone in which it is anchored), relative to the proximal phalanx 18, before osseous union is complete.

The locking cap 102 is placed onto the first end 119 of the wire 118, with the wire 118 received in the first bore 112. The locking cap 102 is moved along the shaft 121 toward the second end 120, decreasing a distance between the locking cap 102 and the second end 120. The stem portion 110 passes through the skin 8 and subcutaneous tissue 12 via a small incision in the skin 8 and subcutaneous tissue 12 until the locking cap 102 is compressed against the distal phalanx 14, with the anti-rotation feature 117 abutting the distal phalanx 14, decreasing rotational instability of the system. The anti-rotation feature 117 may be anchored in the outer cortical bone layer of the distal phalanx 14. The locking cap 102 is moved along the shaft 121 toward the second end 120 until a desired level of compression is reached between the middle phalanx 16 and the proximal phalanx 18.

The set screw 122 is actuated in the second bore 114, contacting and pressing the wire 118 against the locking cap 102 within the first bore 112. This locks the locking cap 102 in place, restricting motion of the joints between the distal phalanx 14, the middle phalanx 16, and the proximal phalanx 18, providing compression between the middle phalanx 16 and the proximal phalanx 18, and providing rotational stability. Once osseous fixation occurs (for example, fusing the joint between the middle phalanx 16 and the proximal phalanx 18), fixation system 100 may be removed.

In the present example, osseous union is to occur between the middle phalanx 16 and the proximal phalanx 18, leaving the distal phalanx 14 free to articulate with the middle phalanx 16. In alternative embodiments, the osseous fixation system 100 may be used to promote osseous union between the distal phalanx 14 and the middle phalanx 16 in addition to or in alternative to between the middle phalanx 16 and the proximal phalanx 18. In other examples, the system 100 (or modified versions thereof) may be used for arthrodesis for other joints of the body, or for fracture repair between two bone fragments that are to be secured back together.

Returning to the example of FIG. 8, when the stem portion 110 is inserted percutaneously into the skin 8 via a small incision (not shown) and abuts the distal phalanx 14, the chamfered portion 108 resides outside the skin 8 and subcutaneous tissue 12 and the body 106 likewise remains outside the skin 8 and subcutaneous tissue 12.

A method of removal of system 100 may include one or more of the following steps: making an incision in the skin 8 and subcutaneous tissue 12 adjacent to the system 100 to facilitate access to the set screw 122 and manipulation of the locking cap 102, loosening the set screw 122 in the second bore 114 to release the shaft 121 of the wire in the first bore 112, removing the threaded second end 120 from the bone, then withdrawing the system 100 from the distal phalanx 14, the middle phalanx 16, the proximal phalanx 18, the skin 8, and the subcutaneous tissue 12. During the removal, the stem portion 110 is withdrawn from the skin 8 and the anti-rotation feature 117 is dislodged from contact with the distal phalanx 14.

Other methods may be used during removal including, but not limited to, removal of the entire locking cap 102 from the wire and skin before removal of the wire 118 or repositioning of the locking cap 102 to aid in removal of the wire 118. In another method of removal, the locking cap 102 may be grasped and employed as a handle to unscrew the threads 123 of the wire 118 from the cortical bone in which it is embedded. This may be done without loosening the set screw 122, or alternatively, by loosening the set screw 122, moving the locking cap 102 proximally on the wire 118 so that the locking cap 102 is easier to grip, and then re-tightening the set screw 122 so that torque is transmitted from the locking cap 102 to the wire 118. The locking cap 102 may then be rotated, for example, by hand, to withdraw the threads of the threaded second end 120 from engagement with the interior bone of the proximal phalanx 18. Then, the system 100 may be distracted by grasping the locking cap 102 (for example, by hand or with a suitable gripping tool such as a set of pliers) and withdrawing the system 100 from the proximal phalanx 18, the middle phalanx 16, the distal phalanx 14, and finally, the skin 8 and subcutaneous tissue 12. Once the system 100 has been removed with any method, the incision may be closed, for example, with sutures, staples, and/or sterile tape.

FIGS. 7 and 8 illustrate use of the bone fixation system 100 inserted into the distal, middle, and proximal phalanx of a toe. As such, the system 100 and method described herein may be used as shown to correct a hammertoe condition. In other applications within the scope of the disclosure, the system and method disclosed herein may be used to immobilize and/or promote osseous union between two or more bones or bone fragments such as phalanges, metatarsals, tarsal, carpals, metacarpals, or any other bones, and/or bone portions or bone fragments.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the present disclosure.

While specific embodiments and applications of the present disclosure have been illustrated and described, it is to be understood that the appended claims are not limited to the precise configuration and components disclosed herein. Various modifications, changes, and variations which will be apparent to those skilled in the art may be made in the arrangement, operation, and details of the methods and systems of the present disclosure disclosed herein without departing from its spirit and scope.

What is claimed is:

1. A method for fixation of a first bone portion relative to a second bone portion through use of a system comprising a wire, a cap, and a fastener, wherein the method comprises:
   inserting the wire percutaneously through the first bone portion and into the second bone portion, the wire having a first end, a threaded second end and a shaft;
   anchoring the threaded second end of the wire in the second bone portion;
   placing the cap onto the first end of the wire such that the wire is slidably received in a first bore of the cap, wherein the cap further comprises a second bore transverse to, and in communication with, the first bore;

moving the cap along the wire toward the threaded second end of the wire to decrease a distance between the cap and the threaded second end of the wire, and to compress the cap against the first bone portion;

actuating the fastener within the second bore to contact the shaft and fix a position of the wire relative to the cap; and after osseous union of the first bone portion to the second bone portion has occurred:

actuating the fastener out of contact with the wire; and withdrawing the threaded second end from the second bone portion and from the first bone portion.

2. The method of claim 1, wherein the fastener is a set screw.

3. The method of claim 1, wherein the shaft comprises a substantially smooth outer surface between the first end and the threaded second end.

4. The method of claim 1, wherein:

the shaft comprises a shaft diameter between the first end and the threaded second end; and the threaded second end comprises a major thread diameter that is less than or equal to the shaft diameter.

5. The method of claim 1, wherein:

the cap further comprises a body portion and a subcutaneous portion; and the method further comprises:

moving the cap along the wire such that the subcutaneous portion passes through a skin and subcutaneous tissue portion and contacts the first bone portion and the body portion remains outside the skin and subcutaneous tissue portion.

6. The method of claim 1, wherein:

the cap further comprises a body portion and a subcutaneous portion comprising one or more anti-rotation features configured to contact the first bone portion; and the method further comprises:

moving the cap along the wire such that the subcutaneous portion passes through a skin and subcutaneous tissue portion and the one or more anti-rotation features engage the first bone portion.

7. The method of claim 6, wherein engaging the one or more anti-rotation features with the first bone portion prevents rotation of the cap relative to the first bone portion.

8. A method for fixation of a first bone portion relative to a second bone portion through use of a system comprising a wire, a cap, and a fastener, wherein the method comprises:

inserting the wire percutaneously through the first bone portion and into the second bone portion, the wire having a first end, a threaded second end, and a shaft comprising a substantially smooth outer surface between the first end and the threaded second end;

anchoring the threaded second end of the wire in the second bone portion;

placing the cap onto the first end of the wire such that the substantially smooth outer surface of the wire is slidably received in a first bore of the cap, wherein the cap further comprises a second bore transverse to, and in communication with, the first bore;

moving the cap along the wire to contact the first bone portion and compress the first bone portion against the second bone portion;

actuating the fastener within the second bore to contact the substantially smooth outer surface of the wire and fix a position of the wire relative to the cap within the first bore.

9. The method of claim 8, wherein the fastener is a set screw.

10. The method of claim 8, wherein after osseous union of the first bone portion to the second bone portion has occurred:

actuating the fastener out of contact with the substantially smooth outer surface of the wire;

withdrawing the cap from the wire; and withdrawing the threaded second end from the second bone portion and from the first bone portion.

11. The method of claim 8, wherein:

the shaft comprises a shaft diameter between the first end and the threaded second end;

the threaded second end comprises a major thread diameter that is less than or equal to the shaft diameter.

12. The method of claim 8, wherein:

the cap further comprises a body portion and a subcutaneous portion; and the method further comprises:

moving the cap along the wire such that the subcutaneous portion passes through a skin and subcutaneous tissue portion and contacts the first bone portion and the body portion remains outside the skin and subcutaneous tissue portion.

13. The method of claim 8, wherein:

the cap further comprises a body portion and a subcutaneous portion comprising one or more anti-rotation features configured to contact the first bone portion; and the method further comprises:

moving the cap along the wire such that the subcutaneous portion passes through a skin and subcutaneous tissue portion and the one or more anti-rotation features engage the first bone portion.

14. The method of claim 13, wherein engaging the one or more anti-rotation features with the first bone portion prevents rotation of the cap relative to the first bone portion.

15. A method for fixation of a first bone portion relative to a second bone portion through use of a system comprising a wire, a cap, and a fastener, wherein the method comprises:

inserting the wire percutaneously through a skin and subcutaneous tissue portion, through the first bone portion and into the second bone portion, the wire having a first end, a threaded second end, and a shaft comprising a substantially smooth outer surface between the first end and the threaded second end;

anchoring the threaded second end of the wire in the second bone portion;

placing the cap onto the first end of the wire such that the substantially smooth outer surface of the wire is slidably received in a first bore of the cap, wherein the cap further comprises:

a body portion comprising a first diameter, a subcutaneous portion comprising a second diameter, and a second bore transverse to, and in communication with, the first bore;

moving the cap along the wire such that the subcutaneous portion passes through the skin and subcutaneous tissue portion and contacts the first bone portion and the body portion remains outside the skin and subcutaneous tissue portion;

actuating the fastener within the second bore to contact the substantially smooth outer surface of the wire and fix a position of the wire relative to the cap within the first bore.

16. The method of claim 15, wherein the fastener is a set screw.

17. The method of claim 15, wherein:
the shaft comprises a shaft diameter between the first end and the threaded second end;
the threaded second end comprises a major thread diameter that is less than or equal to the shaft diameter.

18. The method of claim 15, wherein after osseous union of the first bone portion to the second bone portion has occurred:
actuating the fastener out of contact with the substantially smooth outer surface of the wire;
withdrawing the cap from the wire;
withdrawing the threaded second end from the second bone portion; and
withdrawing the wire from the first bone portion.

19. The method of claim 15, wherein:
the subcutaneous portion further comprises one or more anti-rotation features configured to contact the first bone portion; and
the method further comprises:
engaging the one or more anti-rotation features engage with the first bone portion.

20. The method of claim 19, wherein engaging the one or more anti-rotation features with the first bone portion prevents rotation of the cap relative to the first bone portion.

* * * * *